(12) United States Patent
Schmidt et al.

(10) Patent No.: US 8,199,877 B2
(45) Date of Patent: Jun. 12, 2012

(54) THERAPY FACILITY

(75) Inventors: Roland Schmidt, Erlangen (DE); Stefan Setzer, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 133 days.

(21) Appl. No.: 12/700,941

(22) Filed: Feb. 5, 2010

(65) Prior Publication Data

US 2010/0202587 A1 Aug. 12, 2010

(30) Foreign Application Priority Data

Feb. 6, 2009 (DE) .................. 10 2009 007 856

(51) Int. Cl.
*A61N 5/10* (2006.01)

(52) U.S. Cl. .......................................... 378/65; 378/101

(58) Field of Classification Search .................... 378/65, 378/62, 101, 114
See application file for complete search history.

(56) References Cited

U.S. PATENT DOCUMENTS

| | | | |
|---|---|---|---|
| 5,471,516 A * | 11/1995 | Nunan | 378/65 |
| 5,940,469 A | 8/1999 | Hell et al. | |
| 6,445,766 B1 | 9/2002 | Whitham | |
| 6,459,762 B1 | 10/2002 | Wong et al. | |
| 6,990,175 B2 | 1/2006 | Nakashima et al. | |
| 7,242,742 B2 | 7/2007 | Calderon et al. | |
| 2003/0076927 A1 | 4/2003 | Nakashima et al. | |
| 2007/0018111 A1 | 1/2007 | Calderon et al. | |
| 2010/0014638 A1 * | 1/2010 | Oreper et al. | 378/65 |

* cited by examiner

*Primary Examiner* — Hoon Song
(74) *Attorney, Agent, or Firm* — Schiff Hardin LLP

(57) ABSTRACT

A therapy system has a therapeutic system that produces x-ray radiation and is directed to a treatment area, and an image-producing imaging system that produces x-ray radiation and is directed to the treatment area. The therapeutic system has a first accelerator for electrons of a first energy that produces respective x-ray radiation, and the imaging system has a second accelerator for electrons of a second energy. A supply system is connected to and operates the first and the second accelerators, and the first and second supply systems have at least one component.

10 Claims, 1 Drawing Sheet

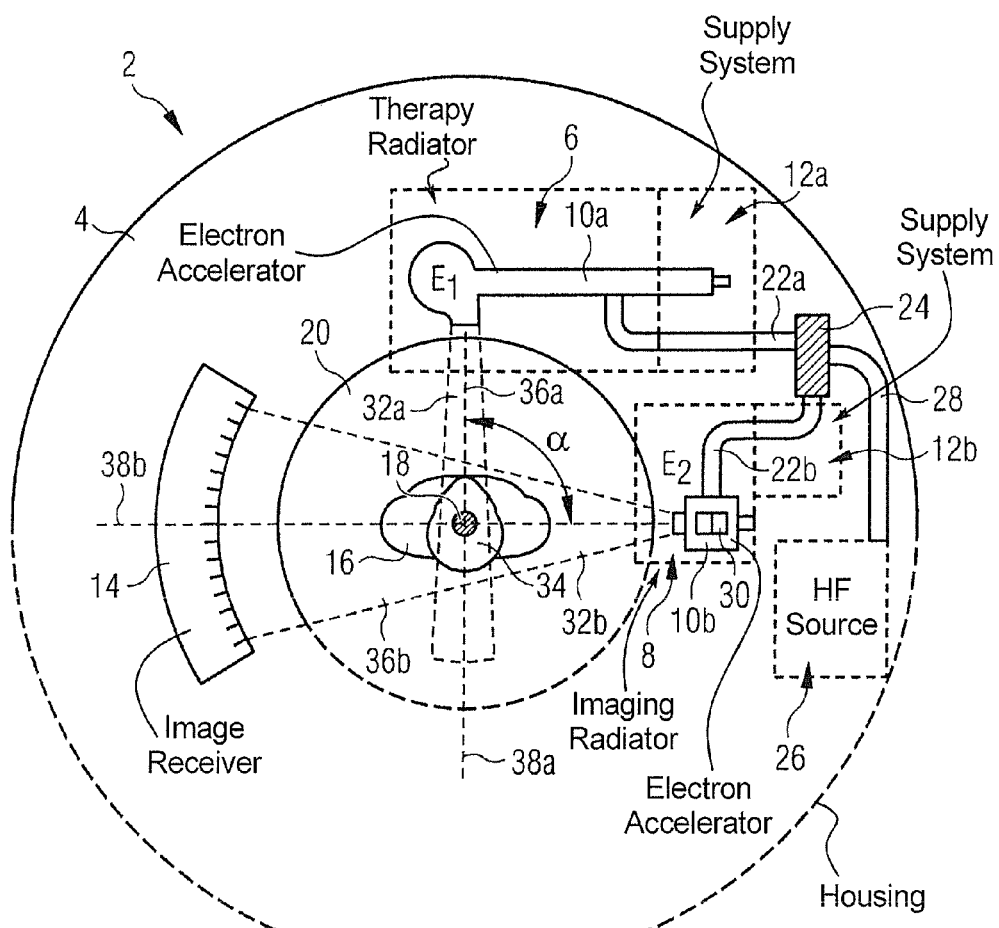

THERAPY FACILITY

BACKGROUND OF THE INVENTION

1. Field of the Invention

The present invention concerns a therapy system of the type having a therapy apparatus that produces therapeutic x-ray radiation.

2. Description of the Prior Art

The x-ray radiation in therapy systems involves energies in the range of approximately 4 to 20 MeV and is used, for example, for tumor radiation of patients. During operation, the radiation is directed to a treatment area of the system in which the patient is placed in the therapy system in such a way that the tumor is located in the treatment area.

By means of CT, MR or PET recordings, it is possible to determine precisely the position of the tumor in the patient. However, at the moment of therapeutic radiation, this position must be brought in alignment with the absolute coordinates or the room or the radiation device, i.e., the therapy system.

In this regard, it is known to produce an x-ray image of the patient once the patient has already been positioned or fixed in the therapy system. The x-ray image should be gene rated immediately prior to therapeutic x-ray radiation. In the case of highly movable tumors, for example, in the stomach or prostate gland of a patient, it is necessary to generate additional images in the continuous radiation cycle even during the period of radiation, in order to monitor the constantly changing location of the tumor and, if required, to reposition the patient.

It is also known to generate an x-ray image of the patient in an imaging system separate from the therapy system and to mark the position of the tumor by marking the skin of the patient. It is a disadvantage that, because of the possible movement of the tumor in relation to the skin of the patient, it is not possible to achieve a precise position in the therapy system.

There are also therapy systems that have additional x-ray tubes and detectors attached to the exterior of the system or its housing. In this way it is possible to obtain an image in parallel with the therapy. In this case, it is a disadvantage that these additional components make it difficult to attend to the patient.

The therapeutic x-ray radiation in the therapy system is produced by an electron accelerator, the energy of which usually can be controlled. It is also known to reduce the beam energy of the electron accelerator of the therapy system as far as possible and to perform so-called MV imaging (megavoltage imaging). Consequently, in order to produce an x-ray image the therapeutic x-ray beam is used which usually has energies in the MeV range. In this case, it is a disadvantage that energies below approximately 1 MeV are almost impossible with the specified electron accelerators. Therefore, x-ray radiation used for imaging is highly energetic, i.e., the image quality is not ideal and shows low contrast in displaying the soft tissue of the tumor tissue.

It is also known to immobilize the patient. This increases the reproducibility of the marked positions, for example on the skin of the patient, and also increases the possibility that the originally adjusted position of the patient is maintained during the treatment. However, this method cannot compensate any movement of the tumor in the patient and is therefore primarily used for tumors in the head region. In this case, it is a disadvantage that the patient usually feels uncomfortable.

In this regard, it is known to synchronize rapid or general movements of the tumor in the patient through gating, i.e., movement or location triggering of the therapeutic x-ray radiation. In this case, it is of disadvantage that such gating is inadequate with tumors in several organs, as, for example, in the intestines. This approach also results in an extension of the treatment time.

SUMMARY OF THE INVENTION

An object of the invention is to provide an improved therapy system.

The invention is based on the basic idea of permanently integrating an x-ray based imaging system into the therapy system, in addition to the therapy apparatus, instead of operating it only as an additional system. According to the invention, in addition to the electron accelerator for the therapeutic x-ray radiation, which is subsequently called first accelerator and which is exclusively used for therapy, a second electron accelerator, which is exclusively used for imaging, is integrated into the therapy system.

While the first accelerator produces electrons of a first, usually relatively high, energy appropriate for therapy, the second accelerator produces electrons of a second, usually low, energy appropriate for imaging. Generally even the capacity of the first accelerator is considerably higher than that of the second.

In this way, the electrons can have appropriate energies for therapy and imaging purposes, respectively, in order to perform the therapy as well as the imaging process with high quality. The same applies to the respective dosage rates.

Consequently, according to the invention, the therapy system has an imaging system that is directed to the treatment area, this imaging system operates also on an x-ray basis.

The imaging system is suitable for proper positioning of the patient during tumor radiation, or for the purpose of exactly determining the position of the tumor in the patient at the moment of treatment, in order to be able to place it with high precision in the treatment area. To each electron accelerator, a supply system is attached that operates the respective accelerator or supplies it with respective energies. According to the invention, the first and the second supply systems connected to the respective accelerators have at least one mutual component. In other words, the fact that the supply of the accelerators takes place at least partially from a mutual supply system saves costs and efforts.

Since a supply system for the first accelerator is already available, and at least parts of the first accelerator can be used as a supply system for the second accelerator, the imaging system requires relatively few components in the therapy system and can be inserted in a space-saving manner.

With regard to image quality, the use of a second accelerator designed in such a way that it uses low electron energy can be compared to a customary x-ray tube.

Integrating a second accelerator in the therapy system avoids costly mechanical and electromechanical attachments of separate x-ray sources including DC generators and controls. Nevertheless, imaging functionality is directly integrated into the therapy system. Since the second accelerator is only used for imaging it can have very small dimensions.

It is therefore not required to find compromise solutions to adjust the energies, etc. of the first accelerator used for imaging to the otherwise high dosage rate output produced for the therapy. Consequently, the first accelerator remains unaffected and can be designed in an optimum fashion with regard to producing therapeutic x-ray radiation. It is possible to keep the dosage output of the second accelerator considerably lower than that of the first accelerator that is used for imaging.

The presence of two accelerators makes it possible to separate the therapy system and the imaging system. As a result both accelerators can be used parallel for different purposes in the sense of function separation. This allows for time-independent, for example, simultaneous or alternating radiation and imaging of the patient, i.e., also a constant tracing of the location of the tumor or repositioning of the patient during radiation. This increases the treatment capacity of the therapy system and increases also the quality of the therapeutic x-ray radiation.

The activation of the second accelerator, that is the imaging accelerator, takes place by means of a separate injector unit or supply system or a separate controlled supply. Consequently, the imaging system can produce x-ray radiation independent from the first accelerator. Such x-ray radiation is produced before and during the operation, or during operation breaks of the first accelerator. The x-ray images thus produced can be continuously analyzed during the treatment of the patient and can be coordinated with the radiation plan.

In a preferred embodiment of the invention, the supply systems are HF supply systems. The respective HF supply of these HF supply systems, i.e., the HF source and its connection to the accelerators, comprise a mutual component. For example, it is possible to use a single HF source, or the connecting line between source and accelerator can have mutual components.

In an embodiment of the model mentioned above, the supply systems actually comprise a mutual HF source, which is then connected with the accelerators by means of wave guides and a wave guide junction. For example, only one magnetron or klystron system is required as HF source, the junction can consist of a wave guide, for example a hollow conductor junction. In other words, the therapy system has a single supply system for both accelerators. The supply system has a junction in order to supply the first, as well as the second accelerator.

In the therapy system, the wave guide in particular can comprise a hollow conductor or a coaxial wave guide system.

In a preferred embodiment, the second accelerator can be constructed of a few, for example one to three cavities. It is easy and inexpensive to produce a respective accelerator.

In a further embodiment, the second accelerator can be one that can produce electron energies of up to a maximum of 3 MeV. Especially preferred is an embodiment of the accelerator that has an operating point for electron energies of 1 MeV or less, for example, in the usual x-ray range of between 40 kV and 200 kV.

In a preferred embodiment, the two accelerators in the therapy system are arranged offset at an angle with regard to the treatment area. In other words, the beam directions of the respective x-ray radiations, which are produced by the accelerators, are offset at said angle. The angle is selected in such a way that the second accelerator and/or an x-ray receiver of the x-ray system, which x-ray receiver is located opposite the second accelerator with regard to the treatment area, is outside of a ray beam of the therapeutic x-ray radiation. In other words, with regard to their x-ray beam directions, the two accelerators are arranged toward each other in such a way that at least the detector of the x-ray system is not captured by the therapeutic x-ray radiation but is primarily irradiated by the x-ray radiation of the lower energetic imaging beam.

Because of the offset arrangement of the imaging system to the therapeutic x-ray beam, accelerator and/or detector of the x-ray system are not damaged by the high therapeutic x-ray radiation required for patient treatment, since they are outside of the x-ray radiation field used for tumor treatment.

In an especially suitable way, the two accelerators are offset by 90° with regard to their x-ray beam directions. In other words, they intersect in the treatment area.

In a preferred embodiment, the therapy system has a tubular housing that surrounds the treatment area at least partially and that includes the therapy system and the imaging system. This results in a compact therapy system which combines in one housing both functionalities of therapeutic radiation and imaging.

BRIEF DESCRIPTION OF THE DRAWING

The single FIGURE schematically illustrates a therapy system in accordance with the present invention, in operation.

DESCRIPTION OF THE PREFERRED EMBODIMENTS

The FIGURE shows a therapy facility 2 having a tubular or circular housing 4 in which a therapy radiation 6 and an imaging radiation 8 have been arranged. The therapy radiator 6 has a first accelerator 10a for electrons, and is supplied by a fist supply system 12a, which supplies the first accelerator 10a with energy, and which controls and operates the first accelerator 10a. The imaging radiator 8 has a second accelerator 10b, which is operated by a respective supply system 12b, and irradiates an image receiver 14 in the form of a detector for the purpose of producing x-ray images.

The FIGURE shows the therapy system in operation. For this purpose a patient 16 has been placed for therapeutic radiation of his tumor 18 in a central opening 20 of the housing 4 or the therapy system 2.

For the transport of energy in the form of HF waves, the supply systems 12a, b have hollow conductors which are connected to the respective accelerators 10a, b. The hollow conductors are attached separately to the respective supply systems 12a, 12b. However, both systems also comprise mutual components, namely a component 24 in the form of a wave guide feeding the hollow conductors 22a, 22b, a mutual HF source 26 and a hollow conductor 28 leading from the HF source to the component 24. The second accelerator 10b of the imaging system 8 comprises two cavities 30.

During operation the second accelerator 10b of the imaging radiator 8 first of all produces a second ray beam 32b of x-ray radiation 36b which x-rays with x-ray radiation 36b a treatment area 34 located in the center of the therapy system 2, as well as the surrounding area. For this purpose, the accelerator produces electrons of a second energy E2.

With regard to positioning, the patient 16 is roughly positioned in the therapy system 2 in such a way that a tumor 18 is located in or as close as possible in the treatment area. By generating an x-ray image by means of the image receiver 14, the actual position of the tumor is displayed in the therapy system 2. By means of this image and with the knowledge of the geometric position of the treatment area 34, as well as the knowledge of the imaging geometry of the imaging radiation and the image receiver 14, the patient can be positioned more precisely so that the tumor 18 can actually be situated in the center of the treatment area 34.

Then the first accelerator 10a produces x-ray beams 36a in a first ray beam 32a which basically covers only the treatment area 34 with a first energy E1, which is clearly higher than the energy E2 of the x-ray radiation used for imaging. This guarantees that, as far as possible, only the tumor 18 is radiated with therapeutic x-ray radiation 36a and not other body parts of the patient 16.

In order to protect the components of the imaging radiator 8 from the x-ray radiation 36a, the imaging radiator 8 or its beam direction 38b is offset by the angle α, for example 90°, with regard to the beam direction 38a of the first x-ray radiation 36a. However, the beam directions intersect in the treatment area 34 so that radiation as well as imaging can take place there.

Although modifications and changes may be suggested by those skilled in the art, it is the intention of the inventors to embody within the patent warranted hereon all changes and modifications as reasonably and properly come within the scope of their contribution to the art.

We claim as our invention:

1. A therapy system comprising:
   a therapeutic x-ray radiation radiator configured to emit therapeutic x-ray radiation that interacts with tissue in a treatment area of a subject to discernibly physiologically modify said tissue;
   an imaging x-ray radiation radiator, separate from said therapeutic x-ray radiator, that emits imaging x-ray radiation that interacts with tissue in the treatment area solely by attenuation of said imaging x-ray radiation by said tissue in the treatment area;
   each of said therapeutic x-ray radiation radiator and said imaging x-ray radiation radiator being oriented relative to the treatment area to irradiate the treatment area with said therapeutic x-ray radiation and said imaging x-ray radiation, respectively;
   an imaging radiation detector disposed at a side of said treatment area opposite from said imaging x-radiation radiator that detects said imaging x-ray radiation after attenuation thereof by said tissue in said treatment area;
   a first electron accelerator that emits electrons at a first energy, said first electron accelerator being connected only to said therapeutic x-ray radiation radiator, said therapeutic x-ray radiation radiator being configured to interact with said electrons at said first energy to produce said therapeutic x-ray radiation;
   a second electron accelerator that emits electrons at a second energy, said second electron accelerator being connected only to said imaging x-ray radiation radiator, and said imaging x-ray radiation radiator being configured to interact with said electrons at said second energy to produce said imaging x-ray radiation;
   a first electrical supply system connected to and operating said first electron accelerator;
   a second electrical supply system connected to and operating said second electron accelerator; and
   said first and second electrical supply systems sharing at least one mutual component.

2. A therapy system as claimed in claim 1 wherein each of said first and second supply systems is a high frequency (HF) supply system comprising an HF source, said HF source being said shared, mutually component.

3. A therapy system as claimed in claim 2 wherein said first supply system comprises a first waveguide connecting said HF source to said therapeutic x-ray radiator, and said second supply system comprises a second waveguide connecting said HF source to said imaging x-ray radiation radiator.

4. A therapy system as claimed in claim 3 wherein each of said first waveguide and said second waveguide is a hollow conductor.

5. A therapy system as claimed in claim 3 wherein each of said first waveguide and said second waveguide is a coaxial waveguide.

6. A therapy system as claimed in claim 1 wherein said second accelerator system comprises a cavity that participates in generating said x-rays at said second energy.

7. A therapy system as claimed in claim 1 wherein said second electron accelerator has a maximum energy of three MeV.

8. A therapy system as claimed in claim 1 wherein said therapeutic x-ray radiation therapeutic x-ray radiation radiator is separated from said imaging x-ray radiation radiator so that at least one of said second electron accelerator and said radiation detector is situated outside of said therapeutic x-ray radiation emitted by said therapeutic x-ray radiation radiator.

9. A therapy system as claimed in claim 8 wherein said angle is a right angle.

10. A therapy system as claimed in claim 1 comprising a generally tubular housing surrounding said treatment area, said tubular housing enclosing at least a portion of said therapeutic x-ray radiation radiator and said first electron accelerator connected therewith, and also enclosing at least a portion of said imaging x-ray radiation radiator and said second electron accelerator connected therewith.

* * * * *